(12) United States Patent
Conlon et al.

(10) Patent No.: US 10,537,724 B2
(45) Date of Patent: Jan. 21, 2020

(54) INJECTION DEVICE

(71) Applicant: GLIDE PHARMACEUTICAL TECHNOLOGIES LIMITED, Abingdon, Oxfordshire (GB)

(72) Inventors: Colin Conlon, Bray (IE); Derek Fenlon, Bray (IE); Pascal Launois, Bray (IE); Martina Moyne, Bray (IE); Owen William Ryan, Bray (IE)

(73) Assignee: ENESI PHARMA LIMITED, Abingdon (GB)

( * ) Notice: Subject to any disclaimer, the term of this patent is extended or adjusted under 35 U.S.C. 154(b) by 140 days.

(21) Appl. No.: 15/548,250

(22) PCT Filed: Feb. 2, 2016

(86) PCT No.: PCT/GB2016/050226
§ 371 (c)(1),
(2) Date: Aug. 2, 2017

(87) PCT Pub. No.: WO2016/124903
PCT Pub. Date: Aug. 11, 2016

(65) Prior Publication Data
US 2018/0028798 A1    Feb. 1, 2018

(30) Foreign Application Priority Data

Feb. 2, 2015   (GB) .................................. 1501697.5

(51) Int. Cl.
*A61M 37/00*      (2006.01)
(52) U.S. Cl.
CPC ..... *A61M 37/0069* (2013.01); *A61M 2205/19* (2013.01); *A61M 2250/00* (2013.01)

(58) Field of Classification Search
CPC .......... A61M 37/0069; A61M 2250/00; A61M 2205/19
See application file for complete search history.

(56) References Cited

U.S. PATENT DOCUMENTS

| 4,576,591 A | 3/1986 | Kaye et al. |
| 6,190,350 B1 * | 2/2001 | Davis ................ A61M 37/0069 604/61 |

(Continued)

FOREIGN PATENT DOCUMENTS

| EP | 1044032 | 10/2000 | |
| WO | WO-9933512 A2 * | 7/1999 | ................ A61J 1/00 |

(Continued)

OTHER PUBLICATIONS

International Search Report for PCT/GB2016/050226, dated Apr. 29, 2016, 6 pages.

(Continued)

*Primary Examiner* — Amber R Stiles
(74) *Attorney, Agent, or Firm* — Nixon & Vanderhye, P.C.

(57) ABSTRACT

An injection device for injecting a solid dose formulation into a human or animal body, the injection device comprising an actuator (10) having a cassette mounting portion (14); a cassette holder (20) having a cassette storage portion; and a cassette selectively movable between the cassette storage portion and the cassette mounting portion, wherein, the cassette (34) comprises a solid dose formulation and the actuator is receivable in the cassette holder to selectively move the cassette between the cassette storage portion and the cassette mounting portion.

10 Claims, 4 Drawing Sheets

(56) References Cited

U.S. PATENT DOCUMENTS

| | | |
|---|---|---|
| 2009/0234374 A1 | 9/2009 | Gabel et al. |
| 2009/0234380 A1 | 9/2009 | Gabel et al. |
| 2010/0000412 A1* | 1/2010 | Heikamp ............. B01D 46/003 96/189 |
| 2012/0016315 A1 | 1/2012 | Radmer et al. |
| 2012/0175810 A1* | 7/2012 | Blaskovich .......... A61K 9/0024 264/255 |
| 2014/0004022 A1* | 1/2014 | Sagona ................ C23C 16/045 422/558 |

FOREIGN PATENT DOCUMENTS

| | | |
|---|---|---|
| WO | WO 2004/014468 | 2/2004 |
| WO | WO 2009/016161 | 2/2009 |

OTHER PUBLICATIONS

Written Opinion of the ISA for PCT/GB2016/050226, dated Apr. 29, 2016, 10 pages.

* cited by examiner

INJECTION DEVICE

This application is the U.S. national phase of International Application No. PCT/GB2016/050226 filed 2 Feb. 2016, which designated the U.S. and claims priority to GB Patent Application No. 1501697.5 filed 2 Feb. 2015, the entire contents of each of which are hereby incorporated by reference.

An injection device particularly suited for, but not explicitly for, injecting a solid dose formulation into a human or animal body.

Solid dose formulations can be introduced into a human or animal body at either low velocity through injection or high velocity fired from a rifle. High velocity dosing is not appropriate for introducing a solid dose formulation into a human body hence substantial efforts have been made to develop a solid dose formulation having the requisite shape and material properties to facilitate ease of injection into a human body. In some cases, solid dose formulations can be introduced into a human body by methods as simple as pushing the solid dose formulation through the skin without aid of a tool or device.

However, in order to avoid causing undue damage to the human body it is desirable to introduce a solid dose formulation by applying only the force necessary for the solid dose formulation to penetrate the human body. Human skin has a relatively low strength hence it is easy to apply too great a force to the solid dose formulation using manual application methods alone.

Use of a tool or device to introduce a solid dose formulation into a human body is known. Typically a tool, or a portion of such a tool, requires to be disposed of after a single use for hygiene and sanitation purposes. The tool, or portion thereof, should be disposed of in such a manner that it is destroyed by means of incineration or otherwise. This can be problematic as many medical tools or devices are constructed from materials with high temperature melting points. Medical tools and devices are also expensive to manufacture and therefore disposal is undesirable.

The use of an actuator and cassette to inject a solid dose formulation into a human body is known. Such an actuator and cassette is described in PCT/EP2003/007859 which is hereby incorporated by reference.

It has been recognised that patients, in some circumstances, do not use injection devices in the correct manner if left to follow instructions provided with the injection device. A demonstration on how to use an injection device has been shown to reduce errors made by patients in using injection devices. However, known injection devices typically require the patient to handle a cassette which contains a solid dose formulation. Any handling can compromise sterility of the cassette and the solid dose formulation leading to potential infection at an injection site.

The present invention seeks to address the aforementioned problems.

An aspect of the invention provides an injection device for injecting a solid dose formulation into a human or animal body, the injection device comprising an actuator having a cassette mounting portion; a cassette holder having a cassette storage portion; and a cassette selectively movable between the cassette storage portion and the cassette mounting portion, wherein, the cassette comprises a solid dose formulation and the actuator is receivable in the cassette holder to selectively move the cassette between the cassette storage portion and the cassette mounting portion.

The injection device of the present invention eliminates the need for a user to handle the cassette thus maintaining sterility of the cassette. Preventing a user from handling the cassette also significantly reduces user error in use of the injection device. The cassette of the present invention can be disposed of separately to the actuator and/or cassette holder.

The cassette storage portion may comprise a plurality of releasable retaining elements for selectively retaining the cassette. The cassette mounting portion may comprise a bayonet fitting for receiving the cassette. The bayonet fitting of the cassette mounting portion and the releasable fastening elements of the cassette storage portion may be co-operable such that rotation of the actuator in the cassette holder releases the releasable fastening elements to facilitate selective movement of the cassette between the cassette storage portion and the cassette mounting portion.

The bayonet fitting of the cassette mounting portion may comprise a locking mechanism for locking the cassette to the bayonet fitting.

The locking mechanism is advantageous in that the cassette is prevented from being inadvertently detached from the actuator before actuation.

The cassette holder may comprise a cassette holder body and a cassette holder insert, the cassette holder insert being removable from the cassette holder body and defining the cassette storage portion. The cassette holder insert may be disposable.

The actuator may be re-usable.

A further aspect of the invention provides a method of injecting a solid dose formulation into a human or animal body, the method comprising: a) providing an injection device comprising an actuator, a cassette holder and a cassette, the cassette comprising a solid dose formulation b) selectively moving the cassette from the cassette holder to the actuator, c) operating the actuator to inject the solid dose formulation into a human or animal body and d) selectively moving the cassette from the actuator to the cassette holder for disposal.

A further aspect of the invention provides a method of injecting a solid dose formulation into a human or animal body, the method comprising: a) providing an injection device comprising an actuator, a cassette holder and a cassette, the cassette comprising a solid dose formulation, b) aligning the actuator with the cassette holder, c) inserting the actuator into the cassette holder to engage the cassette, d) rotating the actuator relative to the cassette holder to lock the cassette to the actuator, e) withdrawing the actuator from the cassette holder, f) injecting the solid dose formulation into a human or animal body, g) aligning the actuator with the cassette holder, h) inserting the actuator into the cassette holder and i) rotating the actuator to lock the cassette to the cassette holder.

Certain embodiments of the inventions are shown in the figures as described below:

The certain embodiments will now be described by way of reference to the figures.

Figure 1:
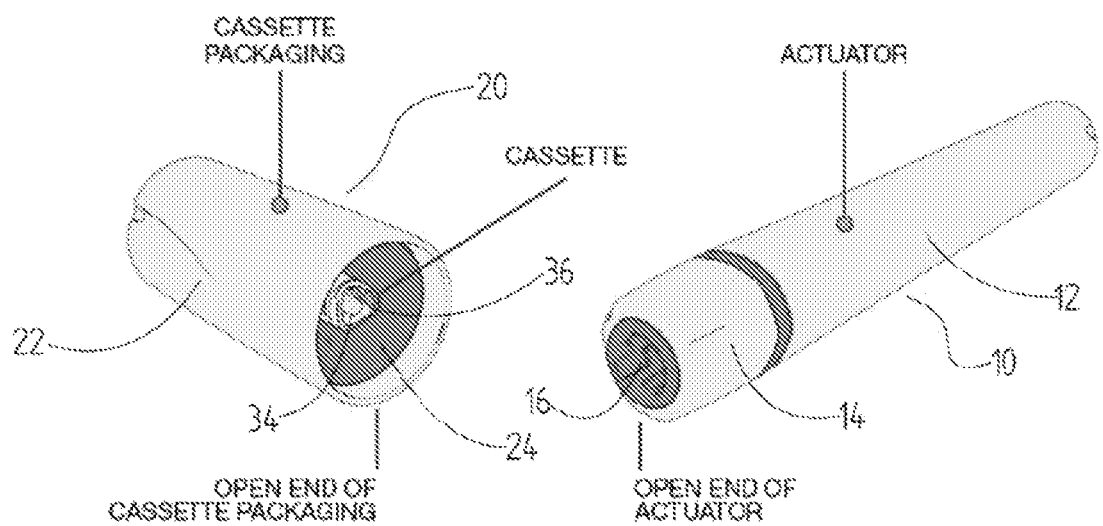
FIG. 1 shows illustrative views of an injection device according to the present invention comprising an actuator assembly and a cassette holder.

Referring to FIG. 1, an actuator assembly 10 and cassette holder 20 are provided for injecting a solid dose formulation into a human or animal body.

The actuator assembly 10 comprises a body portion 12 and a cassette mounting portion 14. The body portion 12 houses a mechanism for operating the actuator. The cassette mounting portion 14 is configured to receive a cassette 34 comprising a solid dose formulation into a bayonet type fitting 16, or similar.

Figure 2:
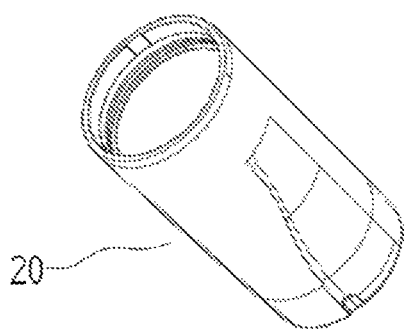
FIG. 2 shows a detailed view of the cassette holder of FIG. 1.
Figure 3:
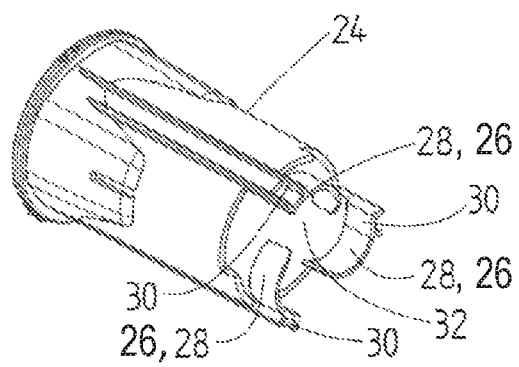
FIG. 3 shows a detailed view of a cassette holder insert which is insertable into the cassette holder.

As shown in FIG. 2, the cassette holder 20 comprises a cassette holder body 22 which is open at one end. A cassette holder insert 24 is insertable into the open end of the cassette holder body 22. The insert 24 comprises a cassette storage portion 26 which stores the cassette 34. The cassette storage portion 26 is defined by three curved prongs 28 which are biased to urge against the cassette 34 to hold it in position. The cassette holder body 22 and insert 24 are made from plastic in one embodiment but the cassette holder 20 could also be made from metal. In one embodiment the cassette holder body 20 and insert 24 are disposable. In other embodiments only the cassette holder insert 24 is disposable.

A plurality of cassette holders can be stored in a sterile packaging such as a vacuum formed packaging with individually removable seals. Alternatively, each individual cassette holder can have its own vacuum formed packaging, for example, and each packaged cassette holder can be stored in a non-sterile container In use, the actuator assembly 10 is axially aligned with the cassette holder 20. The cassette mounting portion 14 of the actuator assembly 10 is inserted into the cassette holder 20. The dose cassette mounting portion is co-operable with the curved prongs 28 of the insert 24 such that rotation of the actuator assembly 10 through sixty degrees in a pre-defined direction causes the actuator assembly 10 to act against curved prongs 28 and displace them relative to the cassette held therebetween. The cassette 34 is then released by the curved prongs 28 and retained by the bayonet fitting 16. The actuator assembly 10 can only be rotated through a maximum angle of approximately sixty degrees. Rotation is limited by a stop (not shown) defined on either the actuator assembly 10 or within the cassette storage portion 26.

The cassette 34 comprises a dosing end (not shown) and a mounting end 3). The mounting end 36 of the cassette 34 protrudes outwardly from the cassette holder insert 24. The mounting end 36 of the cassette 34 comprises a bayonet type fitting, or similar, which is co-operable with the bayonet type fitting 16 of the cassette mounting portion 14 of the actuator assembly 10. When the actuator assembly 10 is withdrawn from the cassette holder insert 24, the cassette 34 is retained by the bayonet fitting 16 of the actuator assembly 10.

The dosing end of the cassette 34 comprises the solid dose formulation and is exposed when the cassette 34 is retained by the actuator assembly 10.

To inject the solid dose formulation into a human or animal body, the cassette 34 is held against the skin at ninety degrees therefrom. The actuator assembly 10 is pushed downwards until an audible click can be heard. The click signifies that the actuator mechanism has operated and injected the solid dose formulation from the cassette 34 through the skin and into the human or animal body. Once the solid dose formulation has been injected, the actuator assembly 10 is withdrawn directly from the injection site.

After the solid dose formulation has been injected into a human or animal body the actuator assembly 10 is axially aligned with the cassette holder 24. The Cassette mounting portion 14 of the actuator assembly 10 is inserted into the cassette holder 20 after use. Rotation of the actuator assembly 10 through sixty degrees causes it to act against the three prongs 28 of the cassette holder insert 24. The actuator assembly 10 can only be rotated through a maximum angle of approximately sixty degrees. Rotation is limited by a stop (not shown) defined on either the actuator assembly 10 or within the cassette storage portion 26. The three prongs 28 are resiliently biased in a position in which they hold the cassette 34 in place. The three prongs 28 are displaced by application of a compressive or torsional force to enable the cassette to enter or exit a space defined between the prongs 28. Once the cassette 34 has entered the space between the prongs 28, the prongs 28 revert to their unstressed configuration and retain the cassette 34. The dosing end of the cassette is orientated away from the open end of the cassette holder body 22. The cassette holder 20 and/or cassette holder insert 24 is then discarded in a safe manner.

Injection devices were tested to evaluate handling of cassettes by users. The following table sets out the sample data set used for the evaluation:

TABLE 1

| # | Age | Predominant Hand | Known Dexterity Issues | Primary Insertion Site |
|---|---|---|---|---|
| 1 | 40 | Right | Received physio for shoulder-90% recovered | Upper Thigh |
| 2 | 40 | Right | None | Abdomen |
| 3 | 45 | Left | None | Abdomen |
| 4 | 51 | Right | None | Upper Thigh |
| 5 | 42 | Left | None | Upper Thigh |
| 6 | 47 | Right | None | Abdomen |
| 7 | 60 | Left | None | Abdomen |
| 8 | 42 | Left-ambi | None | Upper Thigh |
| 9 | 63 | Right | None | Upper Thigh |
| 10 | 59 | Left | Visible deformity to hands-not diagnosed | Abdomen |
| 11 | 53 | Right | Swollen index finger-limited movement | Abdomen |
| 12 | 55 | Left | Locked wrist-limited grip, left arm/hand weaker | Upper Thigh |
| 13 | 65 | Right | None | Upper Thigh |
| 14 | 65 | Right | None | Abdomen |
| 15 | 57 | Right | None | Abdomen |
| 16 | 45 | Right | None | Upper Thigh |
| 17 | 55 | Right | None | Upper Thigh |
| 18 | 64 | Right | Arthritis in fingers | Abdomen |
| 19 | 54 | Right | Arthritis | Abdomen |
| 20 | 64 | Right | Op on elbow-affects grip over long periods of time | Upper Thigh |
| 21 | 64 | Right | Osteo-athritis | Upper Thigh |
| 22 | 63 | right | Right wrist locks up | Abdomen |

Figure 4:
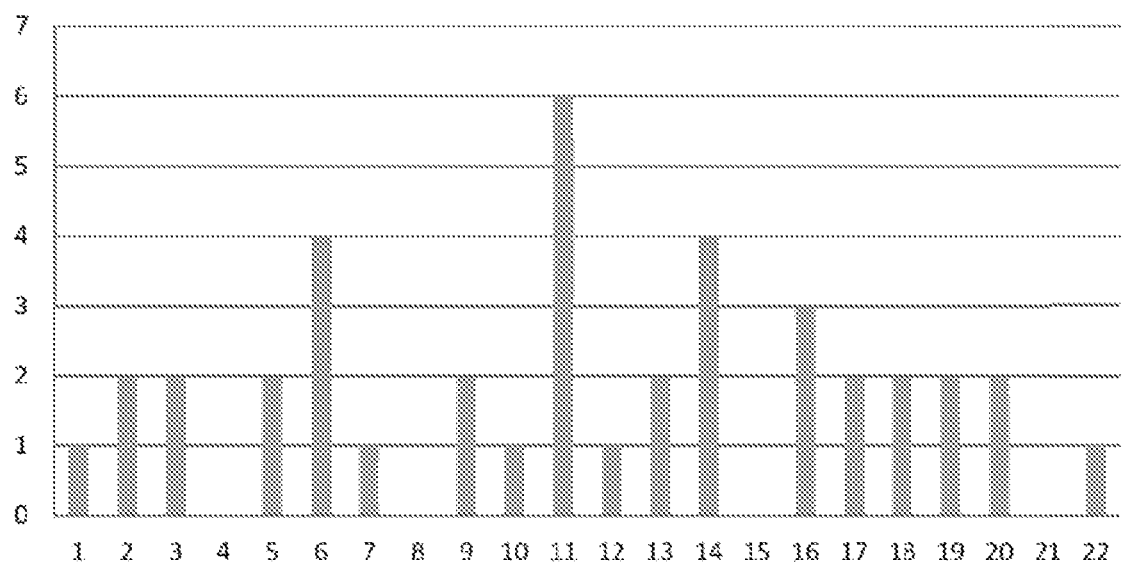
FIG. 4 shows a graph of the number of errors made per patient when using a prior art injection device for the first time without receiving a demonstration prior to first use.

For each patient, age, predominant hand, known dexterity issues and primary injection site were recorded. Each patient was asked to use an injection device following instructions provided with the device and the number of errors made by each patient in using the device were recorded (as summarised in FIG. 4).

Figure 5:
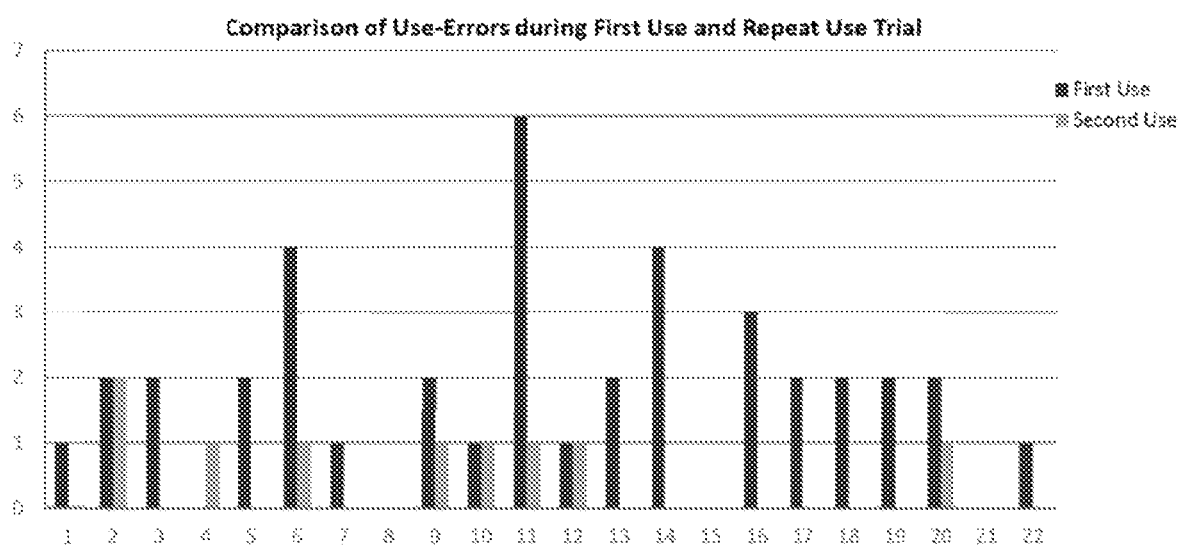
FIG. 5 shows a graph comparing the number of errors made per patient when using the device for the first time without a demonstration prior to first use and after receiving a demonstration prior to second use.

The majority of errors occurred when the user handled the cassette. Each user was then given a demonstration on how to use the device and the errors made were compared with the first use trial (as summarised in FIG. 5). The number of errors observed in the repeat use trial dropped 77.5% in comparison to the first use trial. The evaluation thus indicated that there was a clear issue of patients using injection devices in an incorrect manner when left to follow the instructions provided with the injection device.

The invention claimed is:

1. An injection device for injecting a solid dose formulation into a human or animal body, the injection device comprising:
   an actuator having a cassette mounting portion;
   a cassette holder having a cassette storage portion; and
   a cassette selectively movable between the cassette storage portion of the cassette holder and the cassette mounting portion of the actuator,
   wherein, the cassette comprises a solid dose formulation and the actuator is receivable by the cassette holder to selectively move the cassette between the cassette storage portion and the cassette mounting portion, and the cassette mounting portion comprises a bayonet fitting for receiving the cassette and the bayonet fitting comprises a releasable locking mechanism for locking the cassette to the actuator.

2. An injection device according to claim 1, wherein the cassette storage portion comprises a plurality of releasable retaining elements for selectively retaining the cassette.

3. An injection device according to claim 2, wherein the bayonet fitting of the cassette mounting portion and the releasable retaining elements of the cassette storage portion are co-operable such that rotation of the actuator relative to the cassette holder releases the releasable retaining elements to facilitate selective movement of the cassette from the cassette storage portion to the cassette mounting portion and/or from the cassette mounting portion to the cassette storage portion.

4. An injection device according to claim 3, wherein rotation of the actuator is limited by a stop defined by either the cassette holder or the actuator.

5. An injection device according to claim 3, wherein rotation of the actuator in the cassette holder is limited to sixty degrees in any direction.

6. An injection device according to claim 1 wherein the cassette holder comprises a cassette holder body and a cassette holder insert, the cassette holder insert being removable from the cassette holder body and defining the cassette storage portion.

7. An injection device according to claim 6, wherein the cassette holder is made from plastic.

8. An injection device according to claim 6, wherein the cassette holder insert is disposable and the cassette holder body is re-usable.

9. An injection device according to claim 1 wherein the actuator is a pressure activated actuator which actuates the cassette to inject the solid dose formulation into a human or animal body when an axial force is applied to the actuator in the direction of the human or animal body.

10. An injection device according to claim 1, wherein the actuator is re-usable.

* * * * *